US009426607B2

(12) United States Patent
Shelly et al.

(10) Patent No.: US 9,426,607 B2
(45) Date of Patent: Aug. 23, 2016

(54) AUTOMATIC PAIRING OF WIRELESS PERIPHERALS IN A SYSTEM SUCH AS PRESSURE SUPPORT RESPIRATORY THERAPY SYSTEM

(71) Applicant: KONINKLIJKE PHILIPS N.V., Eindhoven (NL)

(72) Inventors: Benjamin Irwin Shelly, Pittsburgh, PA (US); Jonathan Kurtz, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/646,481

(22) PCT Filed: Dec. 20, 2013

(86) PCT No.: PCT/IB2013/061186
§ 371 (c)(1),
(2) Date: May 21, 2015

(87) PCT Pub. No.: WO2014/097239
PCT Pub. Date: Jun. 26, 2014

(65) Prior Publication Data
US 2015/0289085 A1    Oct. 8, 2015

Related U.S. Application Data

(60) Provisional application No. 61/740,249, filed on Dec. 20, 2012.

(51) Int. Cl.
*H04W 4/00* (2009.01)
*H04W 48/16* (2009.01)
*H04W 8/00* (2009.01)
*A61M 16/06* (2006.01)
*A61M 16/08* (2006.01)
*H04W 76/02* (2009.01)

(Continued)

(52) U.S. Cl.
CPC .......... *H04W 4/008* (2013.01); *A61M 16/0003* (2014.02); *A61M 16/0057* (2013.01); *A61M 16/06* (2013.01); *A61M 16/0875* (2013.01);
(Continued)

(58) Field of Classification Search
CPC ... H04W 76/02; H04W 76/023; H04W 84/20; H04L 67/12; H04L 43/065; H04M 16/0003
See application file for complete search history.

(56) References Cited

U.S. PATENT DOCUMENTS

| 5,148,802 A | 9/1992 | Sanders et al. |
| 5,313,937 A | 5/1994 | Zdrojkowski |

(Continued)

FOREIGN PATENT DOCUMENTS

DE    10116361 A1    10/2002

*Primary Examiner* — Alejandro Rivero

(57) ABSTRACT

An automatic wireless pairing method includes causing a base unit to wirelessly communicate with a number of wireless peripheral devices and wirelessly receive a peripheral device data signal from each of the wireless peripheral devices, wherein the peripheral device data signal received from each of the wireless peripheral devices is based on one or more measurements made by a sensor of the wireless peripheral device, analyzing in the base unit each of the peripheral device data signals, selecting in the base unit one or more of the wireless peripheral devices based on the analyzing of the peripheral device data signals, and responsive to the selecting step, establishing or maintaining wireless communication according to the wireless communications protocol between the base unit and the selected one or more of the wireless peripheral devices and not the wireless peripheral devices other than the selected one or more of the wireless peripheral devices.

13 Claims, 7 Drawing Sheets

(51) Int. Cl.
  *A61M 16/00* (2006.01)
  *H04W 84/20* (2009.01)
  *H04W 84/18* (2009.01)

(52) U.S. Cl.
  CPC .............. *H04W 8/005* (2013.01); *H04W 48/16* (2013.01); *H04W 76/023* (2013.01); *A61M 16/00* (2013.01); *A61M 2016/0027* (2013.01); *A61M 2016/0033* (2013.01); *A61M 2205/3331* (2013.01); *A61M 2205/3584* (2013.01); *A61M 2205/50* (2013.01); *H04W 84/18* (2013.01); *H04W 84/20* (2013.01)

(56) References Cited

U.S. PATENT DOCUMENTS

| | | | |
|---|---|---|---|
| 5,433,193 A | 7/1995 | Sanders et al. | |
| 5,632,269 A | 5/1997 | Zdrojkowski et al. | |
| 5,803,065 A | 9/1998 | Zdrojkowski et al. | |
| 6,029,664 A | 2/2000 | Zdrojkowski et al. | |
| 6,920,875 B1 | 7/2005 | Hill et al. | |
| 7,575,005 B2 * | 8/2009 | Mumford | A61M 16/06 128/205.23 |
| 7,913,689 B2 | 3/2011 | Henry et al. | |
| 8,015,972 B2 * | 9/2011 | Pirzada | G06F 13/409 128/204.18 |
| 2008/0080407 A1 | 4/2008 | Abbate et al. | |
| 2009/0062626 A1 | 3/2009 | Baldus et al. | |
| 2011/0221590 A1 * | 9/2011 | Baker | A61B 5/0002 340/539.12 |
| 2012/0003933 A1 | 1/2012 | Baker et al. | |
| 2012/0134282 A1 | 5/2012 | Tirronen et al. | |
| 2012/0229272 A1 * | 9/2012 | Jacob | A61M 16/06 340/539.12 |
| 2013/0125892 A1 * | 5/2013 | Shelly | A61M 16/00 128/204.23 |
| 2015/0296550 A1 * | 10/2015 | Shelly | A61M 16/00 320/108 |

\* cited by examiner

AUTOMATIC PAIRING OF WIRELESS PERIPHERALS IN A SYSTEM SUCH AS PRESSURE SUPPORT RESPIRATORY THERAPY SYSTEM

CROSS-REFERENCE TO PRIOR APPLICATIONS

This application is the U.S. National Phase application under 35 U.S.C. §371 of International Application Serial No. PCT/IB2013/061186, filed on Dec. 20, 2013, which claims the benefit of U.S. Application Ser. No. 61/740,249, filed on Dec. 20, 2012. These applications are hereby incorporated by reference herein.

BACKGROUND OF THE INVENTION

1. Field of the Invention

The present invention pertains to the wireless pairing of electronic peripheral devices to a base unit device using a wireless protocol such as, without limitation, Bluetooth®, and, in particular, to a method of automatically wirelessly pairing one or more electronic peripheral devices to a base unit based on a signal measured at the base unit and a signal measured at the peripheral devices, for example using correlation analysis of the signals. The concept disclosed herein may be used in any application where a base unit has a sensor that would be expected to show some correlation to a sensor in a peripheral device that will wirelessly connect to the base unit and wherein a simple automatic pairing technique (not employing the concepts of the present invention) may be confused by having multiple peripherals. Such applications may include, without limitation, a positive pressure support therapy system including a base therapy unit and a mask having a peripheral component, such as a wireless pressure sensor, in order to automatically pair the peripheral component with the base unit without confusion. Other possible, alternative applications are described elsewhere herein.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory airflow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory airflow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of a patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the pressure support device with the airway of the patient, so that a flow of breathing gas can be delivered from the pressure/flow generating device to the airway of the patient.

Pressure support therapy systems can be used with one or more peripheral electronic devices that may require data transfer between the peripheral electronic device(s) and the base pressure generating device. For example, and without limitation, it is known to provide a wireless pressure sensor in a mask component of a pressure support therapy system, wherein the wireless pressure sensor is structured to wirelessly communicate pressure information measured by the sensor to the base pressure generating device using a short range wireless communications/data transfer protocol such as, without limitation, the Bluetooth® protocol. Wireless communications/data transfer protocols are desirable and becoming less costly. Wireless data transfer protocols, especially Bluetooth®, typically require pairing between the two devices in question. As is known, such pairing typically requires user intervention.

While automatic pairing is technically feasible, methods to circumvent spurious pairing, for example between a base unit and peripherals that are not in use or between a base unit and peripherals that are in use but with another base unit (e.g. in a sleep lab environment or a home environment having multiple base units) are not adequately addressed in the prior art. Typical cases require the manual selection of a specific peripheral amongst a list of discovered peripherals. Such an environment 1 (e.g. in a sleep lab environment or a home environment having multiple base units) is shown schematically in FIG. 1. As seen in FIG. 1, environment 1 includes two pressure generating device base units 2 and 4, wherein pressure generating device base unit 2 is associated with mask 6 having peripheral device (e.g., wireless pressure sensor) 8 and pressure generating device base unit 4 is associated with mask 10 having peripheral device (e.g., wireless pressure sensor) 12. Thus, in environment 1, the two pressure generating device base units 2 and 4 are in proximity with the two peripheral devices 8 and 12, and both peripherals support wireless communication and are in use. Peripheral device 8 should be paired with pressure generating device base unit 2 and peripheral device 12 should be paired with pressure generating device base unit 4. However, there is no completely automated pairing solution available for this use case in the prior art. For example, a "just works" Secure Simple Pairing protocol may still require user intervention on the base unit, requiring selecting a given peripheral amongst a list of peripherals and having a unique code for a user to find and match amongst the list of peripherals.

SUMMARY OF THE INVENTION

In one embodiment, an automatic wireless pairing method is provided in an environment having a base unit and a plurality of wireless peripheral devices each including a sensor, the base unit and each of the wireless peripheral devices being structured for wireless pairing using a wireless communications protocol. The method includes causing the base unit to at least temporarily wirelessly communicate with one or more of the wireless peripheral devices according to the wireless communications protocol and wirelessly receive a peripheral device data signal from each of the one or more of the wireless peripheral devices, wherein the peripheral device data signal received from each of the one or more of the wireless peripheral devices is based on one or more measurements made by the sensor of the wireless peripheral device, analyzing in the base unit each of the peripheral device data signals, selecting in the base unit at least one of the one or more of the wireless peripheral devices based on the analyzing of the peripheral device data signals, and responsive to the selecting step, establishing or maintaining wireless communication according to the wireless communications protocol between the base unit and the selected at least one of the one or more of the wireless peripheral devices and not the wireless peripheral devices other than the selected at least one of the one or more of the wireless peripheral devices.

In another embodiment, a base unit structured for wireless pairing using a wireless communications protocol with a plurality of wireless peripheral devices each including a sensor is provided. The base unit includes a wireless communications module structured to implement the wireless communications protocol, and a controller coupled to the wireless communications module, the controller storing one or more software routines executable by the controller and structured to: (i) cause the base unit to at least temporarily wirelessly communicate with one or more of the wireless peripheral devices according to the wireless communications protocol and wirelessly receive a peripheral device data signal from each of the one or more of the wireless peripheral devices, wherein the peripheral device data signal received from each of the one or more of the wireless peripheral devices is based on one or more measurements made by the sensor of the wireless peripheral device; (ii) analyze each of the peripheral device data signals; (iii) select at least one of the one or more of the wireless peripheral devices based on the analysis of the peripheral device data signals, and (iv) responsive to selecting one or more of the wireless peripheral devices, establish or maintain wireless communication according to the wireless communications protocol and using the wireless communications module between the base unit and the selected at least one of the one or more of the wireless peripheral devices and not the wireless peripheral devices other than the selected at least one of the one or more of the wireless peripheral devices.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
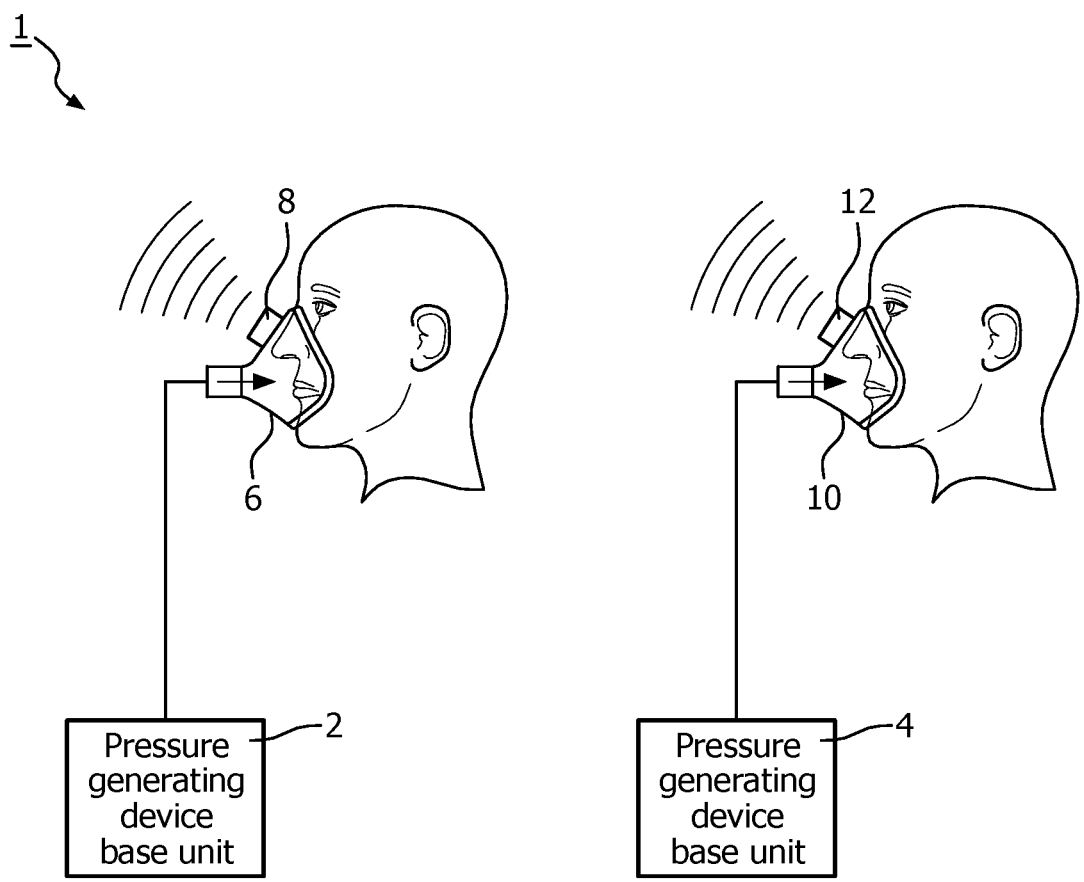
FIG. 1 is a schematic diagram of a prior art environment employing multiple pressure generating device base units and multiple patient interface peripheral devices.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the words "peripheral" and "peripheral device" shall mean any auxiliary electronic device that connects to and works with a base/host computing device in some way.

As used herein, the terms "pair", "pairing" or "paired" shall refer to a condition wherein two electronic devices capable of wireless communication using a predetermined common protocol, such as, without limitation, the Bluetooth® protocol, are communicably and wirelessly linked with one another under the predetermined common protocol.

As used herein, the term "temporarily wirelessly communicate" shall refer to a condition wherein two electronic devices capable of wireless communication using a predetermined common protocol, such as, without limitation, the Bluetooth® protocol, are communicably and wirelessly linked with one another under the predetermined common protocol for a certain limited period of time.

As used herein, the term "discoverable peripheral device" shall mean a peripheral device with which a base/host computing device is able to establish wireless communications using a predetermined common protocol, such as, without limitation, the Bluetooth® protocol.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As described in detail herein in connection with a number of non-limiting exemplary embodiments, a system and methodology are provided wherein a base unit having a base unit sensor and a base unit processing device is provided with software configured to select one or more wireless peripheral devices from amongst a number of discoverable wireless peripheral devices each having a number of associated peripheral sensors, which may be the same as or different from the base unit sensor. The software causes the base unit to pair with each of the discoverable peripheral devices temporarily in order to receive data measured by the peripheral sensor of each discoverable peripheral devices. From the data received from the discoverable peripheral devices, and, in the exemplary embodiment, based on data measured by the base unit sensor, the software determines which peripheral device(s) to it should maintain a wireless communications link/data connection with. For example, the software may perform a correlation analysis using data signals received from each of the paired peripheral devices and a data signal measured by the base unit to determine which peripheral data signal best correlates with the base unit data signal. As described in greater detail herein, the peripheral data signals and the base unit data signal can both be measured passively or, alternatively, can both be measured as a response to an active test condition or stimulus.

Figure 2:
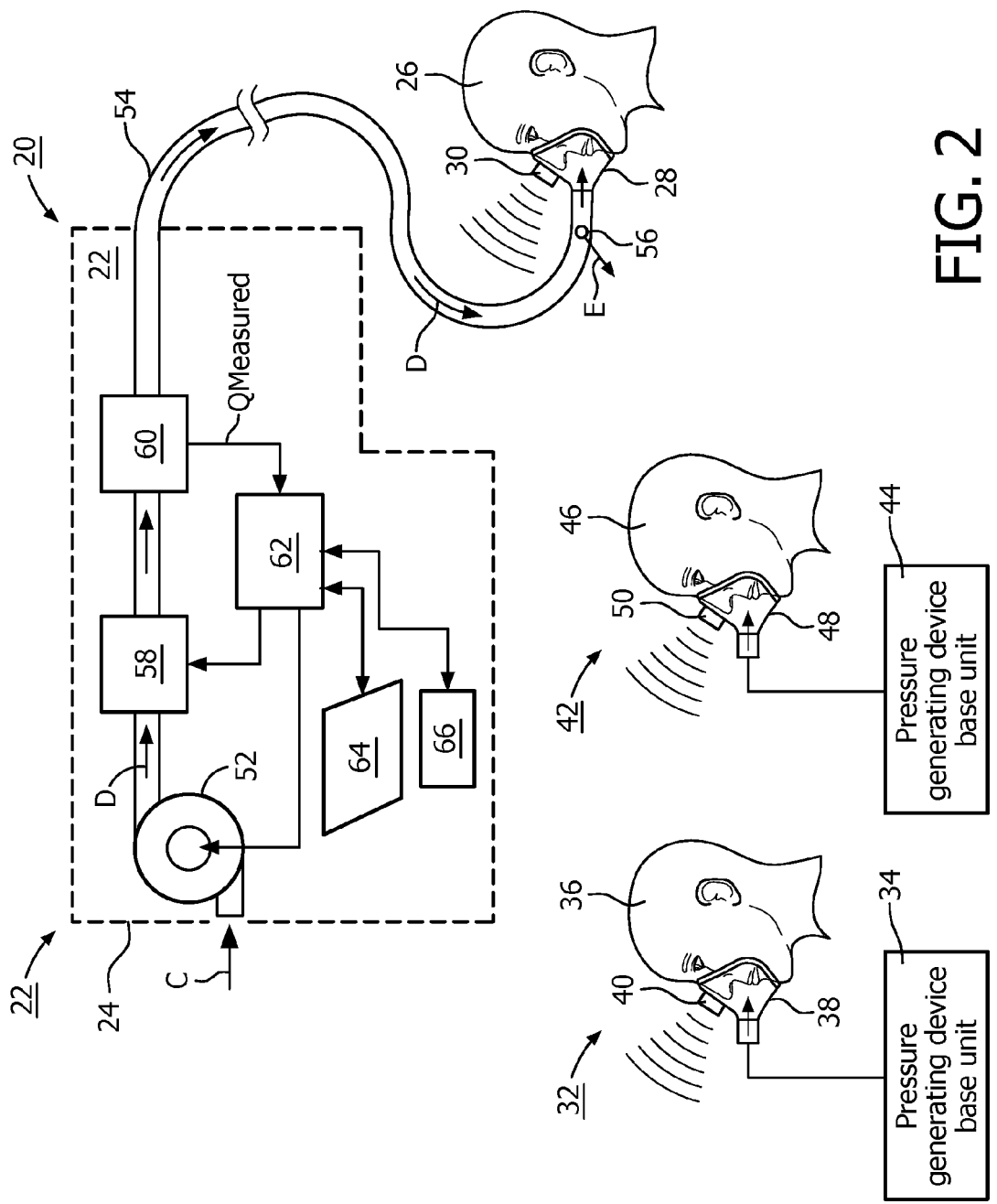
FIG. 2 is a schematic diagram of an environment employing multiple pressure generating device base units and multiple patient interface peripheral devices in which the principles of the present invention may be implemented according to one exemplary embodiment.

FIG. 2 is a schematic diagram of an environment 20 (e.g., a sleep lab environment or a home environment having multiple base units) in which the principles of the present invention may be implemented according to one exemplary embodiment. As seen in FIG. 2, environment 20 includes a first pressure support system 22 having a pressure generating device base unit 24 for delivering a flow of breathing gas to a first patient 26 through a mask 28 having a wireless peripheral device 30. Environment 20 further includes a second pressure support system 32 having a second pressure generating device base unit 34 for delivering a flow of breathing gas to a second patient 36 through a mask 38 having a wireless peripheral device 40, and a third pressure support system 42 having a third pressure generating device base unit 44 for delivering a flow of breathing gas to a third patient 46 through a mask 48 having a wireless peripheral device 50. As was the case with the prior art shown in FIG. 1, each of the pressure generating device base units 22, 34 and 44 is in proximity with each of the wireless peripheral devices 30, 40 and 50, and of the wireless peripheral devices 30, 40 and 50 is in use. However, as described in detail herein, and unlike the prior art, pressure support system 22 implements a methodology according to the present invention for automatic wireless pairing of peripheral devices while avoiding spurious pairing.

Referring to FIG. 2, pressure generating device base unit 24 of pressure support system 22 includes a gas flow generator 52, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway of patient 26 at relatively higher and lower pressures, i.e., generally equal to or above ambient atmospheric pressure. The pressurized flow of breathing gas, generally indicated by arrow D from gas flow generator 52, is delivered via a delivery conduit 54 to mask 28 of any known construction, which is typically worn by or otherwise attached to patient 26 to communicate the flow of breathing gas to the airway of patient 26. Delivery conduit 54 and mask 28 are typically collectively referred to as a patient circuit.

Pressure support system 22 shown in FIG. 2 is what is known as a single-limb system, meaning that the patient circuit includes only delivery conduit 54 connecting patient 26 to pressure generating device base unit 24. As such, exhaust vent 56 is provided in delivery conduit 54 for venting exhaled gasses from the system as indicated by arrow E. It should be noted that exhaust vent 56 can be provided at other locations in addition to or instead of in delivery conduit 54, such as in mask 28. It should also be understood that exhaust vent 56 can have a wide variety of configurations depending on the desired manner in which gas is to be vented from pressure support system 22.

The present invention also contemplates that pressure support system 22 can be a two-limb system, having a delivery conduit and an exhaust conduit connected to patient 26. In a two-limb system (also referred to as a dual-limb system), the exhaust conduit carries exhaust gas from patient 26 and includes an exhaust valve at the end distal from patient 26. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 2, mask 28 is a nasal/oral mask. It is to be understood, however, that mask 28 can be a nasal mask, a pillows style nasal cushion, a cradle style nasal cushion, a full face mask, or any other patient interface device that provides a suitable gas flow communicating function. Also, for purposes of the present invention, the phrase "patient interface" can include delivery conduit 54 and any other structures that connect the source of pressurized breathing gas to patient 26.

In the illustrated embodiment, pressure support system 22 includes a pressure controller in the form of a valve 58 provided in delivery conduit 54. Valve 58 controls the pressure of the flow of breathing gas from flow generator 52 delivered to patient 26. For present purposes, flow generator 52 and valve 58 are collectively referred to as a pressure generating system because they act in concert to control the pressure and/or flow of gas delivered to patient 26. However, it should be apparent that other techniques for controlling the pressure of the gas delivered to patient 26, such as varying the blower speed of flow generator 52, either alone or in combination with a pressure control valve, are contemplated by the present invention. Thus, valve 58 is optional depending on the technique used to control the pressure of the flow of breathing gas delivered to patient 26. If valve 58 is eliminated, the pressure generating system corresponds to flow generator 52 alone, and the pressure of gas in the patient circuit is controlled, for example, by controlling the motor speed of flow generator 52.

Pressure support system 22 further includes flow sensor 60 that measures the flow of the breathing gas within delivery conduit 54. In the particular embodiment shown in FIG. 2, flow sensor 60 is interposed in line with delivery conduit 54, most preferably downstream of valve 58. Flow sensor 60 generates a flow signal $Q_{MEASURED}$ that is provided to controller 62 and is used by controller 62 to determine the rate of flow of gas at patient 26, referred to as $Q_{PATIENT}$. Of course, other techniques for measuring the respiratory flow rate of patient 26 are contemplated by the present invention, such as, without limitation, measuring the flow rate directly at patient 26 or at other locations along delivery conduit 54, measuring patient flow based on the operation of flow generator 52, and measuring patient flow using a flow sensor upstream of valve 58 or of flow generator 52. In addition, it should be noted that other techniques may be used to estimate flow. For example, flow may be estimated using motor parameters (e.g. motor current). Also, most modern pressure support system implementations include pressure sensors, which may be used to control the pressure at the outlet of the device (and, by extension, the pressure at the patient) as well as to perform other monitoring tasks (e.g. monitor acoustic signal for snoring).

Figure 5:
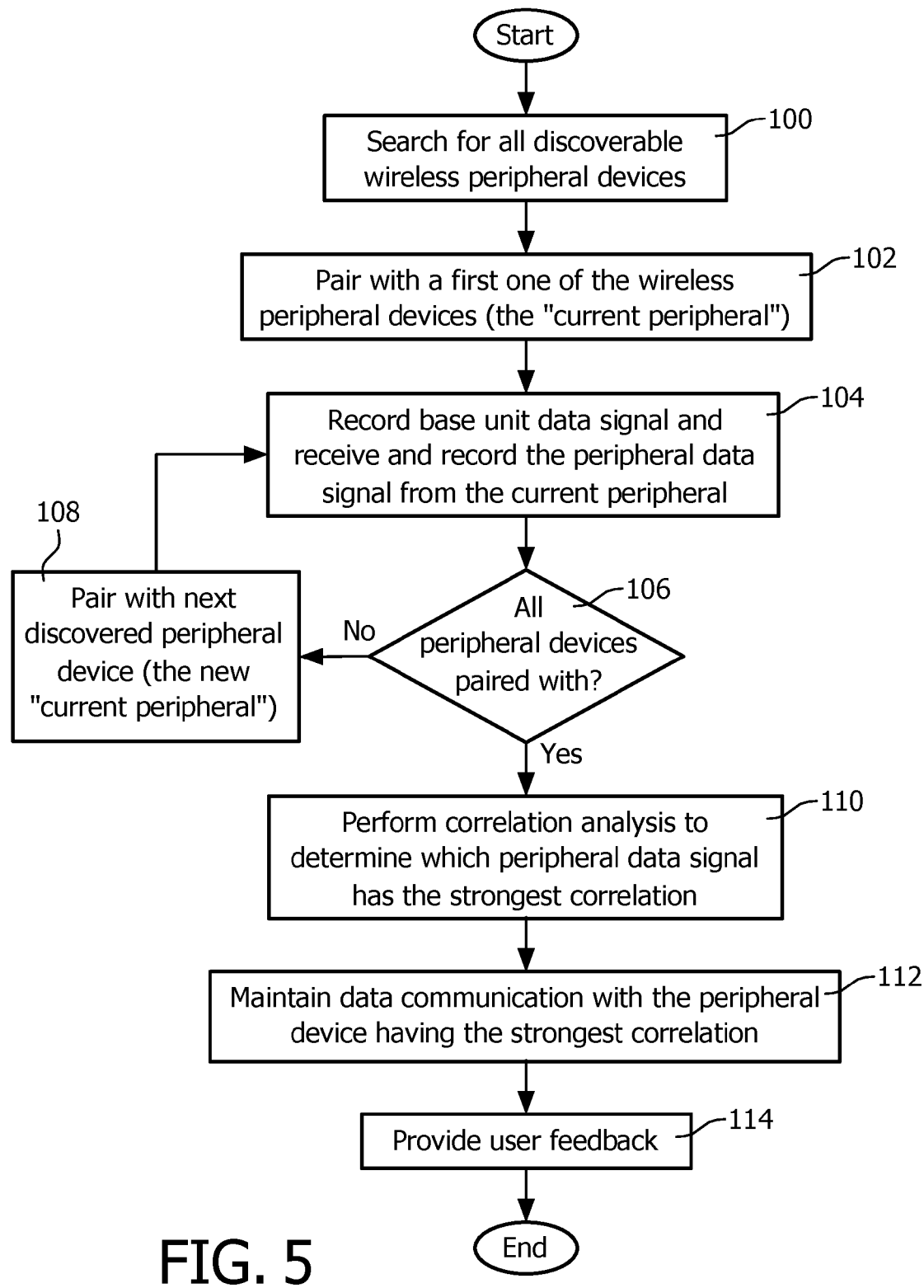
FIGS. 5-7 are flowcharts showing methods of implementing the present invention according to alternative exemplary embodiments.
Figure 6:
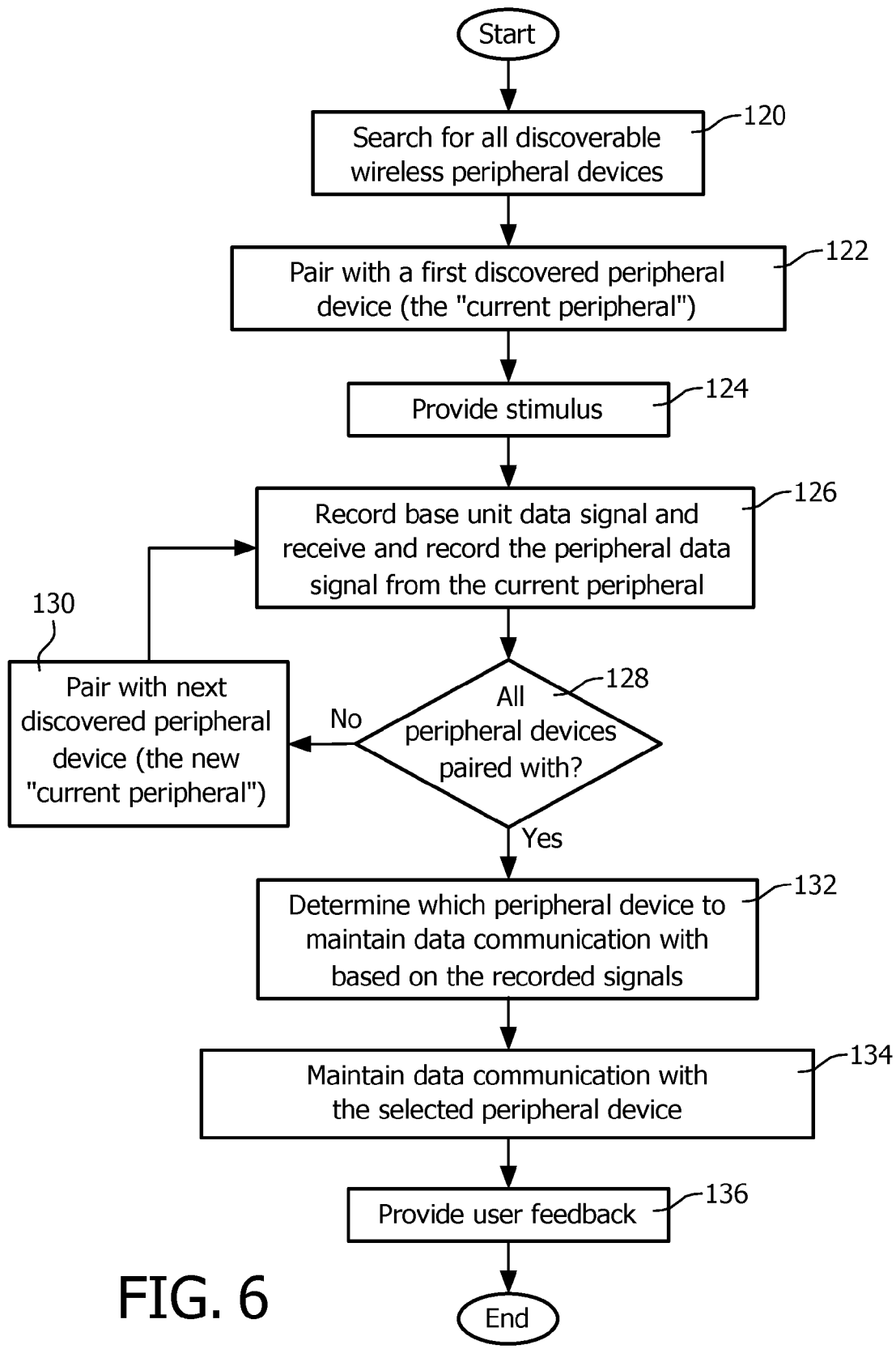
Figure 7:
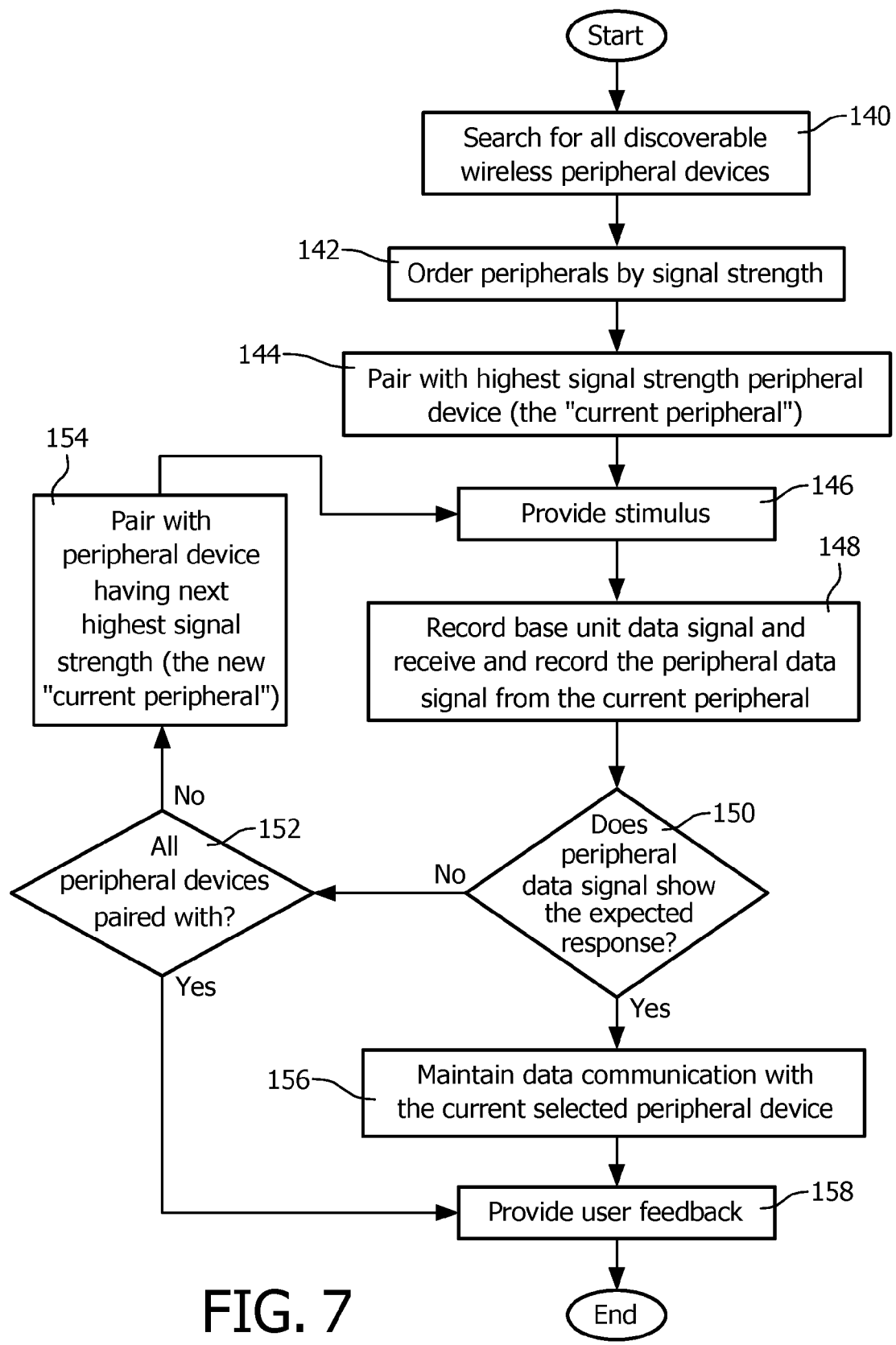

Controller 62 includes a processing unit, such as, for example, a microprocessor, a microcontroller or some other suitable processing device, and a memory (that is provided as part of the processing unit or that is operatively coupled to the processing unit) that provides a tangible storage medium for data and software routines executable by the processing unit for controlling the operation of pressure support system 22 (e.g., the software routines as described herein and as implemented as shown in, for example, FIGS. 5-7). Input/output device 64 is provided for setting various parameters used by pressure support system 22, as well as for displaying and outputting information and data to a user, such as a clinician or caregiver.

In the exemplary embodiment, which is a single-limb system, controller 62 estimates the leakage of gas from pressure support system 22 using any suitable technique and incorporates this leak estimation into the determination of the actual patient flow. This leak estimation is required in a single-limb system, because a single-limb system includes a known leak through the exhaust vent as well as other unknown leaks, such as leaks at the patient contact site of the patient interface and at various conduit couplings on the patient circuit. In a two-limb system, leak estimation may not be required, because a flow sensor is typically provided at the exhaust vent to measure, directly, the flow of exhaust gas. In such a system, the patient flow can be determined by subtracting the measured exhaust flow from the measured flow delivered to the patient. It can be appreciated that leak detection can be performed in a two-limb system to increase the accuracy of the patient flow determination. U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., U.S. Pat. No. 6,029,664 to Zdrojkowski et al., and U.S. Pat. No. 6,920,875 to Hill et al., the contents of each of which are incorporated herein by reference, describe how to accomplish the necessary functions in order to provide separate IPAP and EPAP levels to the patient. These functions include techniques for detecting and estimating leak, and techniques for detecting the respiratory state of a patient (I/E), and managing, e.g., triggering and cycling, the bi-level delivery of breathing gas to the patient in the presence of leaks. Thus, a detailed discussion of these functions is omitted from the present application for the sake of simplicity and brevity.

Finally, pressure support system 22 in the exemplary embodiment includes a short range wireless communications module 66 which is operatively coupled to controller 62. In the exemplary embodiment, short range wireless communications module 66 is a module that is structured and configured to enable pressure support system 22 to communicate with other, similarly equipped electronic devices (e.g., peripheral device 30 as described herein) over a short range wireless network. In the exemplary embodiment, short range wireless communications module 66 is a Bluetooth® module that is structured and configured to enable pressure support system 22 to communicate with other devices over an ad hoc Bluetooth® network. In addition, short range wireless communications module 66 may be incorporated within pressure generating device base unit 24, or may be a module that is selectively connectable to pressure generating device base unit 24 via a USB port or other suitable connection.

Also in the exemplary embodiment, each of the wireless peripheral devices 30, 40 and 50 is a wireless pressure sensor with Bluetooth® communications capabilities, although it will be understood that, as described elsewhere herein, wireless peripheral devices 30, 40 and 50 may be other types of peripheral components, such as, without limitation, an ECG, an EEG, an effort belt or a mask integratable actigraph/accelerometer, pulse oximeter, EtCO2 capnographer, or EOG.

As noted elsewhere herein, pressure generating device base unit 24 is provided with one or more software routines executable by controller 62 that is/are configured to automatically select wireless peripheral device 30 from among all of the discoverable wireless peripheral devices in environment 20 (i.e., wireless peripheral devices 30, 40 and 50). Particular, alternative implementations of such software routines are described elsewhere herein in connection with FIGS. 5, 6 and 7. However, in general, the software: (i) causes pressure generating device base unit 24 to temporarily wirelessly communicate (using short range wireless communications module 66) with each of the discoverable wireless peripheral devices in environment 20 (i.e., wireless peripheral devices 30, 40 and 50) in order to receive sensor data signals measured by those devices, and (ii) performs an analysis (e.g., a correlation analysis) using the data signals received from each of the discoverable peripheral devices and, in the exemplary embodiment, a data signal measured/generated by pressure generating device base unit 24, to determine which discoverable wireless peripheral device is proper for continued pairing (e.g., based on which peripheral data signal best correlates with the base unit data signal). As will be appreciated, and as described in more detail below, in the case of the illustrative environment 20 shown in FIG. 2, the best correlation should be with wireless peripheral device 30, since it is the one that is associated with pressure generating device base unit 24. Once that determination is made, then that pairing will be maintained and the pairings with any other of the other wireless peripheral device (i.e., 40 and 50) will be terminated. The peripheral data signals and the base unit data signal can both be measured passively (e.g., see FIG. 5 implementation) or, alternatively, can both be measured as a response to an active test condition or stimulus (e.g., see FIG. 6 and FIG. 7 implementations).

Figure 3A:
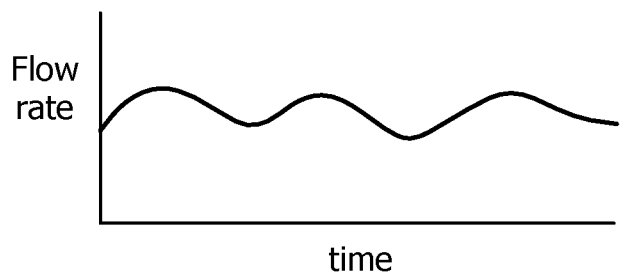
FIGS. 3A-3D illustrate a base unit data signal and peripheral data signals measured passively according to one particular exemplary embodiment of the present invention.
Figure 3B:
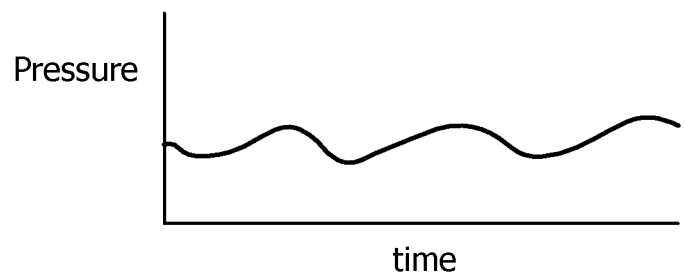
Figure 3C:
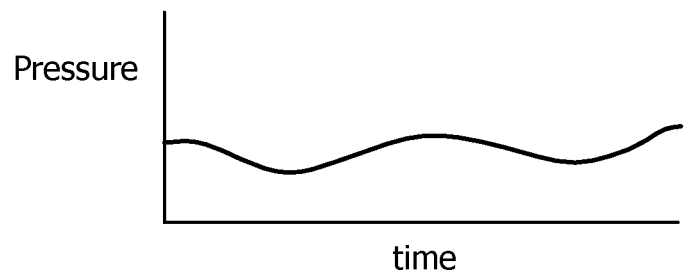
Figure 3D:
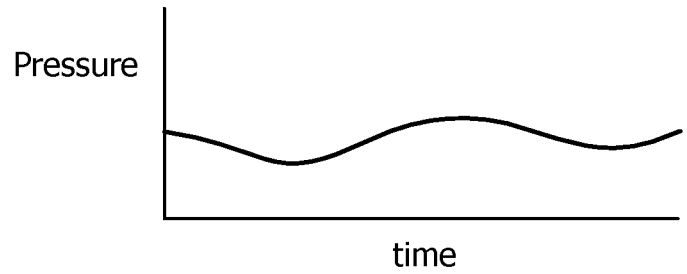

FIGS. 3A-3D illustrate one particular example of how the methodology of the present invention may be implemented in environment 20, wherein the base unit data signal and the peripheral data signals are all measured passively and wherein correlation analysis is employed. In this example, the base unit data signal is shown in FIG. 3A and is a flow signal representing the current rate of gas flow in pressure generating device base unit 24 that is generated based on measurements made by flow sensor 60 (FIG. 2) as described elsewhere herein. Also in this example, each of the wireless peripheral devices 30, 40 and 50 is a wireless pressure sensor that measures the gas pressure at mask 28, 38, 48, respectively, and each of the peripheral data signals is a pressure signal that is generated by the associated wireless peripheral devices 30, 40 and 50 (FIG. 3B shows the signal from wireless peripheral device 30, FIG. 3C shows the signal from wireless peripheral device 40, and FIG. 3D shows the signal from wireless peripheral device 50). Through a number of correlation measures based on the signals of FIGS. 3A-3D, it will evident that the signal of FIG. 3B has a much stronger correlation to the signal of FIG. 3A than the signals of FIGS. 3C and 3D have to the signal of FIG. 3A (the signals of FIGS. 3C and 3D are each at a different frequency than the signal of FIG. 3A in this example and thus have very little correlation with the signal of FIG. 3A). Thus, wireless peripheral device 30 will be selected for continued, ongoing pairing.

In an exemplary embodiment, the correlation analysis is performed using a cross-correlation function to determine a measure of strength of correlation in each case. Other measures of correlation between two signals are known to those skilled in the art and may also be used in implementing the principles of the present invention. Such measures of correlation between two signals may include, without limitation, normalized cross-correlation, coherence, Pearson correlation coefficient, breath rate measurement, sum of multiplication of the two signals at a given (or several) time-shifts, and power at a given frequency (Fourier analysis), as well as other time and frequency domain measures looking for a relationship between the signals.

Figure 4A:
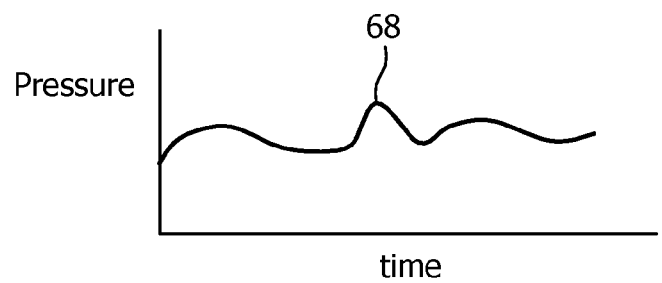
FIGS. 4A-4D illustrate a base unit data signal and peripheral data signals measured in response to a stimulus according to another, alternative particular exemplary embodiment of the present invention.
Figure 4B:
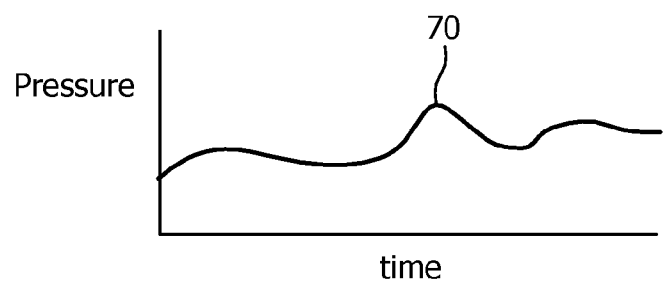
Figure 4C:
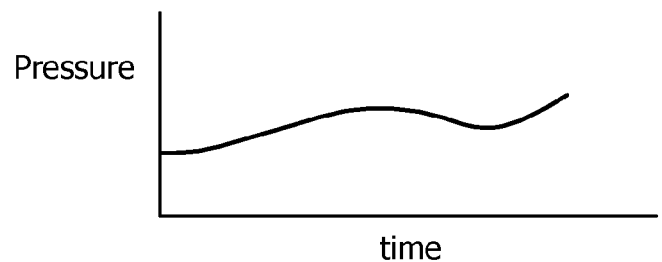
Figure 4D:
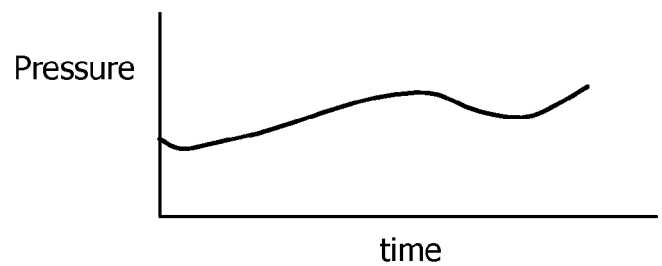

FIGS. 4A-4D illustrate another particular example of how the methodology of the present invention may be implemented in environment 20, wherein the base unit data signal and the peripheral data signals are all measured as a response to an active test condition or stimulus and wherein correlation analysis is employed. In this example, the injected stimulus is a small pressure pulse (e.g., on the order of 2cmH$_2$O) generated by gas flow generator 52. Also in this example, the base unit data signal is shown in FIG. 4A and is a pressure signal generated based on measurements made by a base unit pressure sensor, and each of the peripheral data signals is a pressure signal that is generated by the associated wireless peripheral devices 30, 40 and 50 (FIG. 4B shows the signal from wireless peripheral device 30, FIG. 4C shows the signal from wireless peripheral device 40, and FIG. 4D shows the signal from wireless peripheral device 50). As seen in FIGS. 4A and 4B, the base unit signal shows the injected stimulus at 68, and the peripheral data signal from wireless peripheral device 30 shows the response to the injected stimulus at 70. In addition, as seen in FIGS. 4C and 4D, the signals shown therein (from wireless peripheral devices 40 and 50) do not show a response to the injected stimulus. Thus, it will be evident that the signal of FIG. 4B has a much stronger correlation to the signal of FIG. 4A than the signals of FIGS. 4C and 4D have to the signal of FIG. 4A, and, as a result, wireless peripheral device 30 will be selected for continued, ongoing pairing.

As described above, in the illustrated exemplary embodiment involving an active test condition or stimulus, pressure generating device base unit 24 is structured to measure base unit data signal shown in FIG. 4A including the injected stimulus. In alternative embodiments, pressure generating device base unit 24 may have no ability or need to effectively measure the injected stimulus, but rather pressure generating device base unit 24 (in particular, controller 62) will have knowledge of the injected stimulus and ways to differentiate the peripheral data signals to determine which one represents the proper, expected response to the injected stimulus. For example, the stimulus could be a 5 Hz sine wave with 0.5 cm H$_2$O amplitude, and each of the peripherals could be monitored for power at the 5 Hz frequency during the time of injected stimulus.

In addition, in the illustrated exemplary embodiment, the injected stimulus is a small pressure pulse. In other implementations, the stimulus can be ongoing (such as blower noise, or ongoing small amplitude pressure or flow oscillations, etc.) and may or may not be "intentionally injected" solely for purposes of eliciting a response. A large number of different stimuli from pressure generating device base unit 24 could be conceived of by one skilled in the art.

In alternative implementations, the stimulus is enacted by the peripheral upon being paired with or upon another condition initiated by the base unit and measured by the base unit. This may involve pairing a base unit with a peripheral device that has some control component to it or has the ability to generate a physical output. One example of such a peripheral device is a mask that has a pressure sensor and a valve. When the peripheral module is paired with base unit, the valve could make a "flutter" or small oscillation. A sensor in the base unit could detect the effect of the flutter on the flow and know that it paired with the correct peripheral.

Furthermore, as described above, in the illustrated exemplary embodiments (FIGS. 3A-3D and 4A-4D), the base unit data signals are flow signals and the peripheral data signals are pressure signals. In an alternative implementation, the base unit data signal may be a measure that relates to airflow generated by pressure generating device base unit 24, such as, without limitation, motor PWM duty cycle or motor current. In other implementations, the base unit data signal may be a measure that relates to pressure. It will be appreciated that one skilled in the art could extend this technique to other implementations, using different signals to identify the proper peripheral for continued, ongoing pairing.

FIG. 5 is a flowchart showing a method of automatic pairing that may be implemented by the one or more software routines stored by pressure support system 22 and executable by controller 62 for controlling the operation of pressure support system 22 according to one particular, exemplary embodiment of the present invention. The method shown in FIG. 5 is a method wherein the base unit data signal and the peripheral data signals are all measured passively, and thus may be used to implement the embodiment described in connection with FIGS. 3A-3D. For illustration purposes, the method will be described in connection with environment 20 of FIG. 2.

The method begins at step 100, wherein pressure generating device base unit 24 searches for all discoverable wireless peripheral devices in environment 20 using short range wireless communications module 66 and the associated wireless protocol (Bluetooth® in the present example). As will be appreciated, in the exemplary environment 20, this will result in wireless peripheral devices 30, 40 and 50 being discovered.

Next, at step 102, the pressure generating device base unit 24 pairs with a first one of the discovered wireless peripheral devices (one of 30, 40 and 50) using the appropriate protocol (Bluetooth®) in the present example). In the present discussion, the wireless peripheral device that is paired with is referred to as the "current peripheral" (e.g., wireless peripheral device 30 for illustration purposes). Then, at step 104, the controller 62 records the base unit data signal (e.g., the flow signal based on the measurements made by flow sensor 60 as described herein) and receives and records the peripheral data signal from the current peripheral as measured by the sensor component of that device. At step 106, a determination is made as to whether all of the discovered peripheral devices have been paired with. If the answer is no, then the method proceeds to step 108, wherein pressure generating device base unit 24 pairs with a next one the discovered peripheral devices and the method returns to step 104. As will be appreciated, this portion of the method of FIG. 5 is an iterative process will ensure that pressure generating device base unit 24 temporarily wirelessly communicates with each of the discovered wireless peripheral devices 30, 40 and 50 and, in each case, records the base unit data signal and the peripheral data signal from each peripheral. It will be understood however, that this iterative process that involves pairing to each discovered peripheral sequentially is meant to be exemplary only, and that, instead, pressure generating device base unit 24 may, alternatively, pair to multiple discoverable peripheral devices at a single time to measure the required information (a base unit data signal and the peripheral data signal from each device). Regardless of how this is done, following step 106, data will have been gathered from all of the discoverable peripheral devices 30, 40 and 50. Then, at step 110, a correlation analysis is performed to determine which peripheral data signal has the strongest correlation to the associated base unit data signal. In particular, as described elsewhere herein, a correlation function or functions is used to compare each received and stored peripheral data signal to the associated recorded base unit data signal and the extent of the correlation is determined based upon the particular chosen function or functions (the correlation analysis described may be performed using any of the functions that have been described elsewhere herein, or any other suitable such function that is now known or hereafter developed). As will be appreciated, in the illustrated embodiment, step 110 will result in one of the peripheral data signals and thus one of the discovered wireless peripheral devices 30, 40 and 50 being determined to have the strongest correlation. Next, at step 112, pressure generating device base unit 24 maintains wireless data communication with the wireless peripheral device 30, 40, 50 determined to have the strongest correlation, which in the present example should be wireless peripheral device 30. In the exemplary embodiment, wireless data communication with wireless peripheral device 30 is maintained and the data is used for detection/control/recording until such a point in time where it is no longer desired to stay connected. (e.g. if the signal from the peripheral goes to zero/is disconnected or if the base unit is turned off, etc.) In addition, the temporary wireless data communication with any of the other wireless peripheral devices will be terminated. Then, at step 114, feedback is provided to the user through input/output device 64 indicating to the user that pairing with the appropriate wireless peripheral deice 30 has been completed.

In one particular alternative exemplary embodiment of the method of FIG. 5, during the step of searching for wireless peripheral devices, such devices may provide compatibility information to pressure generating device base unit 24 so that it will only evaluate compatible wireless peripheral devices.

In addition, if following step 110 of FIG. 5 there is no wireless peripheral device that has been determined to have a strong correlation or if the correlation results are not conclusive, all of the discovered wireless peripheral devices (or some subset of such devices) could be tested with a new segment of data (e.g., the test could be run again), could be tested using a different methodology (for example, the methodology employing an injected stimulus as described hereafter in connection with FIGS. 6 and 7), or the user could be prompted on input/output device 64 with an error message, a troubleshooting guide, or some other prompt to manually enter pairing data.

FIG. 6 is a flowchart showing a method of automatic pairing that may be implemented by the one or more software routines stored by pressure support system 22 and executable by controller 62 for controlling the operation of pressure support system 22 according to another particular, alternative exemplary embodiment of the present invention. The method shown in FIG. 6 is a method wherein the base unit data signal and the peripheral data signals are all measured in response to a stimulus, and thus may be used to implement the embodiment described in connection with FIGS. 4A-4D. For illustration purposes, the method will be described in connection with environment 20 of FIG. 2.

The method begins at step 120, wherein pressure generating device base unit 24 searches for all discoverable wireless peripheral devices using short range wireless communications module 66 (using Bluetooth® in the present example). At step 122, after all of the wireless peripheral devices have been discovered, controller 62 causes pressure generating device base unit 24 to pair with a first one of the discovered peripheral devices, referred to as the "current peripheral." Next, at step 124, controller 62 causes pressure generating device base unit 24 to provide a stimulus. As described elsewhere herein, such a stimulus may take on any of a number of different forms. In the present example, the stimulus is in the form of a small pressure pulse generated by flow generator 52. It will be appreciated, however, that other stimuli are also possible. Next, at step 126, controller 62 records the base unit data signal as measured by pressure generating device base unit 24 and receives and records the peripheral data signal from the current peripheral. In the present example, and as described elsewhere herein, the base unit data signal is a flow signal based on the measurements made by flow sensor 60 and the peripheral data signal is a pressure signal as measured by the sensor component of the current peripheral. Next, at step 128, a determination is made by controller 62 as to whether all of the wireless peripheral devices have been paired with. If the answer is no, then the method proceeds to step 130, wherein pressure generating device base unit 24 pairs with a next one of the discovered peripheral devices and the method returns to step 124. Thus, as will be appreciated, this portion of the method of FIG. 6 provides an iterative process wherein all of the discovered wireless peripheral devices will be paired with sequentially and the relevant data will be measured and stored. As discussed elsewhere herein, this is meant to be exemplary only, and it will be understood that pressure generating device base unit 24 can instead pair to multiple wireless peripheral devices at the same time to measure the relevant information.

Regardless of how the pairing is performed, following step 128, pressure generating device base unit 24 will have stored the base unit data signal and the peripheral data signal from each of the discovered peripheral devices. Next, at step 132, controller 62 determines which wireless peripheral device to maintain data communication with based on the recorded signals. In particular, as described in detail elsewhere herein, controller 62 will determine which of the peripheral data signals shows an appropriate response to the provided stimulus (step 124). In the exemplary embodiment, this involves performing a correlation analysis wherein each base unit data signal is compared to each associated recorded peripheral data signal to determine which one has the strongest correlation. Other methods of selecting which wireless peripheral device showed the appropriate response to the stimulus are also possible and have been described elsewhere herein. Thus, following step 132, controller 62 will have selected one of the discovered wireless peripheral devices (30, 40, 50 in the present example) as the wireless peripheral device to which a connection is to be made (in the present example, that should be wireless peripheral device 30). Next, at step 134, pressure generating device base unit 24 maintains data communication with the selected wireless peripheral device, and terminates data communication with respect to all other discovered peripheral devices. Then, at step 136, in the present embodiment, input/output device 64 is utilized to notify the user that the pairing with the appropriate wireless peripheral device has been successfully completed. Again, if a suitable wireless peripheral device is not found as a result of the steps of method of FIG. 6, then the test can be re-run or the user can be prompted with an error message, a troubleshooting guide, or to enter data manually for pairing purposes.

FIG. 7 is a flowchart showing a method of automatic pairing that may be implemented by the one or more software routines stored by pressure support system 22 and executable by controller 62 for controlling the operation of pressure support system 22 according to still another particular, exemplary alternative embodiment of the present invention. The method shown in FIG. 7, like the method shown in FIG. 6, is a method wherein the base unit data signal and the peripheral data signals are measured in response to a stimulus. Thus, the method of FIG. 7 may be used to implement the embodiment described in connection with FIGS. 4A-4D. For illustration purposes, the method will be described in connection of with environment 20 of FIG. 2.

The method of FIG. 7 begins at step 140, wherein pressure generating device base unit 24 searches for all discoverable wireless peripheral devices in environment 20 using short range wireless communications module 66 (and Bluetooth® in the present example). Next, at step 142, controller 62 orders the peripherals based upon the strength of the return signal (or, alternatively, based on another measurable attribute of the signal provided by the peripheral). Then, at step 144, pressure generating device base unit 24 pairs with the peripheral device having the highest signal strength, referred to as the "current peripheral." Next, at step 146, pressure generating device base unit 24 provides a stimulus (such as, without limitation, a small pressure pulse) as described in detail elsewhere herein. At step 148, controller 62 records the base unit data signal and receives and records the peripheral data signal from the current peripheral. Next, at step 150, a determination is made by controller 62 as to whether the peripheral data signal received and recorded from the current peripheral shows the expected response to the stimulus. If the answer at step 150 is no, then, at step 152, controller 162 makes a determination as to whether all of the discovered peripheral devices have been paired with. If the answer is no, then at step 154, pressure generating device base unit 24 pairs with the wireless peripheral device having the next highest signal strength and the method returns to step 146. Thus, as will be appreciated, steps 146 through 154 provide an iterative process wherein the discovered wireless peripheral devices are paired with sequentially based upon the signal strength of each peripheral device and, at step 150, the process is terminated when a wireless peripheral device is found having or showing the response to the stimulus that is expected. In the present example, the wireless peripheral device showing that response should be wireless peripheral device 30 in environment 20.

Referring again to FIG. 7, when the answer at step 150 is yes, the method proceeds to step 156, wherein pressure generating device base unit 24 is caused to maintain data communication with the wireless peripheral device determined to have shown the expected stimulus response. Then, at step 158, feedback is provided to the user as described elsewhere herein. In addition, as will be appreciated, if none of the discovered wireless peripheral devices show the expected response, the method will proceed from step 152 with a yes response to step 158 wherein feedback may be provided to the user using input/output device 64 in the form of an error message, a troubleshooting guide or a prompt to manually enter pairing data.

Thus, FIGS. 5, 6 and 7 show a number of different exemplary methodologies that may be implemented in the software executable by controller 62 of pressure generating device base unit 24 for enabling pressure generating device base unit 24 to automatically pair with the appropriate wireless peripheral device in environment 20 in a manner that avoids or reduces the risk of spurious pairing as described herein.

Furthermore, the techniques described herein can be used to continue to confirm the appropriateness of the data connection between pressure generating device base unit 24 and a given wireless peripheral device or devices (e.g., 30) over time. For example, if a different mask having a different wireless peripheral device is switched to after an initial data connection, it may not be desirable for pressure generating device base unit 24 to continue to maintain data communication with the original wireless peripheral device or to use the data that is provided by the original wireless peripheral device. One or more of the methods that are described herein (e.g. FIG. 5, 6 or 7) can be run at a prompted or a prescheduled time in order to ensure that pressure generating device base unit 24 is using data from the appropriate peripheral. For example, pressure generating device base unit 24 can initialize this at every power on/off, at any monitored patient condition (such as a patient disconnect), every "x" minutes, or every time that a button is pressed. In this additional embodiment, only one discoverable peripheral is necessary and the output of the correlation/test analysis may help determine whether the one peripheral still shows a good correlation (e.g. is still in use with pressure generating device base unit 24). If a poor correlation is found, the user may be prompted to rectify the condition or confirm the disconnection of the initially data connected peripheral.

In alternative embodiments, pressure generating system 22 may be configured to employ multiple wireless peripheral devices, each one having a sensor. For example, pressure generating system 22 may be configured to employ the following three wireless peripheral devices: a hose, a humidifier, and a mask. In one particular embodiment, in environment 20, such multiple wireless peripheral devices are sorted and tested using any of the methods described herein by type (device type information will be communicated to pressure generating device base unit 24 during the pairing process) to ensure that pressure generating system 22 will establish and maintain data communication with only one hose, one humidifier, and one mask.

In still another embodiment, each of the wireless peripheral devices can be tested using more than one of the methods described herein (e.g., each of the methods of FIGS. 5, 6 and 7), with the resulting being input into a weighted or fuzzy decision logic to determine which peripheral(s) to establish/maintain data communication to.

In still other embodiments, the peripheral device data signals may be further processed by controller 62 to determine a desirable attribute or attributes in order to determine a correlation to the base unit data signal.

Still other examples of strong correlation may include the following: (i) a large measure of overall variability in the proximal pressure sensor in response to the base unit blower injecting an amount of white noise, (ii) a high peak-to-peak amplitude on a peripheral pressure sensor in response to a high peak-to-peak flow in the base unit, and (iii) a simple fundamental frequency (and perhaps phase) of respiration monitored by pressure at the mask in response to the same measure at the base unit.

Moreover, it should be noted that while the exemplary embodiment employs the Bluetooth® protocol, it will be understood that the concepts described herein can be used with any wireless technology or with any system wherein a given "base" or "master" needs to choose amongst several "peripheral" or "slave" units.

In addition, in conjunction with the methods described herein, other techniques can be used to allow a specific peripheral (e.g., mask) to be "activated" when it is attached to a base unit such as pressure generating device base unit 24. For example, a circuit can be completed when the mask is attached to a hose or the Bluetooth® circuitry can be set to automatically pair when a sensor in the peripheral detects that the peripheral has been attached to a patient or to a base unit such as pressure generating device base unit 24 (e.g. selective activation techniques, such as activating when a pressure is measured, strain sensor, using a connection point to complete a circuit, etc.) These techniques can significantly limit the number of discoverable peripherals in a given environment, as will ensuring that data connected peripherals are no longer discoverable.

Finally, in still other embodiments, the scheme described herein could be turned on its head, wherein a particular peripheral device, such as a mask, acts as the "master" to provide the functionality of the base or host unit and select amongst multiple units, such as pressure generating (e.g., CPAP) units, which would function as peripheral devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. In an environment having: (i) a pressure generating device base unit of a pressure support system structured to generate a flow of breathing gas for delivery to a patient through a patient interface device, the pressure generating device base unit including a base unit sensor, and (ii) a plurality of wireless peripheral devices each including a sensor and each being either a component of the pressure support system or a component of an additional pressure support system in the environment, wherein the pressure generating device base unit and each of the wireless peripheral devices are structured for wireless pairing using a wireless communications protocol, an automatic wireless pairing method, comprising:

causing the pressure generating device base unit to at least temporarily wirelessly communicate with one or more of the wireless peripheral devices according to the wireless communications protocol and wirelessly receive a peripheral device data signal from each of the one or more of the wireless peripheral devices, wherein the peripheral device data signal received from each of the one or more of the wireless peripheral devices is based on one or more measurements made by the sensor of the wireless peripheral device;

generating in the pressure generating device base unit a number of base unit data signals, wherein each of the base unit data signals is based on one or more measurements made by the base unit sensor;

analyzing in the pressure generating device base unit each of the peripheral device data signals and the number of base unit data signals including performing a correlation analysis in the pressure generating device base unit using each of the peripheral device data signals and the number of base unit data signals;

selecting in the pressure generating device base unit at least one of the one or more of the wireless peripheral devices based on an outcome of the correlation analysis; and responsive to the selecting step, establishing or maintaining wireless communication according to the wireless communications protocol between the pressure generating device base unit and the selected at least one of the one or more of the wireless peripheral devices and not the wireless peripheral devices other than the selected at least one of the one or more of the wireless peripheral devices.

2. The method according to claim 1, wherein the one or more wireless peripheral devices is each of the plurality of wireless peripheral devices.

3. The method according to claim 1, wherein the correlation analysis compares each of the peripheral device data signals to one of the base unit data signals, and wherein each of the selected at least one of the one or more of the wireless peripheral devices is determined to have at least a certain level of correlation to the one of the base unit data signals to which is was compared.

4. The method according to claim 1, wherein the base unit sensor is either a flow sensor or a pressure sensor, wherein each of the base unit data signals is either a flow signal or a pressure signal, wherein each of wireless peripheral devices is a wireless pressure sensor coupled to a mask component, and wherein each of the peripheral device data signals is a pressure signal.

5. The method according to claim 1, wherein the causing step further comprises causing the base unit to generate a predetermined stimulus, and wherein the analyzing step comprises analyzing each of the peripheral device data signals and the number of base unit data signals to determine whether any of the peripheral device data signals exhibits an expected response to the predetermined stimulus, the selected at least one of the one or more of the wireless peripheral devices being those wireless peripheral devices that generated peripheral device data signals exhibiting the expected response.

6. The method according to claim 5, wherein each of the wireless peripheral devices is a wireless pressure sensor coupled to a mask component, wherein each of the peripheral device data signals is a pressure signal, and wherein the predetermined stimulus is a pressure pulse generated by the pressure generating device base unit.

7. The method according to claim 1, wherein the wireless communications protocol is the a Bluetooth protocol.

8. A pressure generating device base unit of a pressure support system structured to generate a flow of breathing gas for delivery to a patient through a patient interface device, the pressure generating device base unit being structured for wireless pairing using a wireless communications protocol with a plurality of wireless peripheral devices each including a sensor, wherein each of the wireless peripheral devices is either a component of the pressure support system or a component of an additional pressure support system in the environment, comprising:
- a base unit sensor;
- a wireless communications module structured to implement the wireless communications protocol; and
- a controller coupled to the wireless communications module, the controller storing one or more software routines executable by the controller and structured to:
- cause the pressure generating device base unit to at least temporarily wirelessly communicate with one or more of the wireless peripheral devices according to the wireless communications protocol and wirelessly receive a peripheral device data signal from each of the one or more of the wireless peripheral devices, wherein the peripheral device data signal received from each of the one or more of the wireless peripheral devices is based on one or more measurements made by the sensor of the wireless peripheral device;
- cause the pressure generating device base unit to generate a number of base unit data signals, wherein each of the base unit data signals is based on one or more measurements made by the base unit sensor;
- analyze each of the peripheral device data signals and the number of base unit data signals including performing a correlation analysis in the pressure generating device base unit using each of the peripheral device data signals and the number of base unit data signals;
- select at least one of the one or more of the wireless peripheral devices based on an outcome of the correlation analysis; and
- responsive to selecting at least one of the one or more of the wireless peripheral devices, establish or maintain wireless communication according to the wireless communications protocol and using the wireless communications module between the pressure generating device base unit and the selected at least one of the one or more of the wireless peripheral devices and not the wireless peripheral devices other than the selected at least one of the one or more of the wireless peripheral devices.

9. The pressure generating device base unit according to claim 8, wherein the correlation analysis compares each of the peripheral device data signals to one of the base unit data signals, and wherein each of the selected at least one of the one or more of the wireless peripheral devices is determined to have at least a certain level of correlation to the one of the base unit data signals to which is was compared.

10. The pressure generating device base unit according to claim 8, wherein the base unit sensor is either a flow sensor or a pressure sensor, wherein each of the base unit data signals is either a flow signal or a pressure signal, wherein each of wireless peripheral devices is a wireless pressure sensor coupled to a mask component, and wherein each of the peripheral device data signals is a pressure signal.

11. The pressure generating device base unit according to claim 8, wherein the one or more software routines are structured to cause the pressure generating device base unit to generate a predetermined stimulus, and to analyze each of the peripheral device data signals and the number of base unit data signals to determine whether any of the peripheral device data signals exhibits an expected response to the predetermined stimulus, the selected at least one of the one or more of the wireless peripheral devices being those wireless peripheral devices that generated peripheral device data signals exhibiting the expected response.

12. The pressure generating device base unit according to claim 11, wherein each of wireless peripheral devices is a wireless pressure sensor coupled to a mask component, wherein each of the peripheral device data signals is a pressure signal, and wherein the predetermined stimulus is a pressure pulse generated by the pressure generating device base unit.

13. The pressure generating device base unit according to claim 8, wherein the wireless communications protocol is the a Bluetooth protocol and wherein the wireless communications module is Bluetooth module.

* * * * *